United States Patent [19]

Johnson

[11] Patent Number: 4,856,532
[45] Date of Patent: Aug. 15, 1989

[54] LARGE-SIGNAL AIRWAY RESISTANCE MEASUREMENT

[76] Inventor: Arthur T. Johnson, R.D. 2, Box 32, Darlington, Md. 21034

[21] Appl. No.: 76,221

[22] Filed: Jul. 22, 1987

[51] Int. Cl.⁴ .............................................. A61B 5/08
[52] U.S. Cl. ................................................... 128/720
[58] Field of Search ........................................ 128/720

[56] References Cited

U.S. PATENT DOCUMENTS

| | | | |
|---|---|---|---|
| 3,036,569 | 5/1962 | Clements et al. | 128/720 |
| 3,857,385 | 12/1974 | Hampl | 128/720 |
| 4,122,839 | 10/1978 | Franetzki et al. | 128/720 |
| 4,220,161 | 9/1980 | Berlin et al. | 128/720 |

OTHER PUBLICATIONS

Johnson et al, "Airflow Perturbation . . . Animals", IEEE Trans Biomed Eng, vol. BME-31, No. 9, Sep. 1984, pp. 622-624.

Johnson, "Conversion . . . Measurements", IEEE Trans Biomed Eng., vol. BME-33, No. 8, Aug. 1986, pp. 803-806.

Primary Examiner—Lee S. Cohen
Attorney, Agent, or Firm—Berman, Aisenberg & Platt

[57] ABSTRACT

A technique is described for converting small-signal measurements of airway resistance to large-signal resistance. In the preferred embodiment, the small-signal measurements are obtained by the use of an airways perturbation device which periodically increases the flow resistance.

6 Claims, 1 Drawing Sheet

LARGE-SIGNAL AIRWAY RESISTANCE MEASUREMENT

TECHNICAL FIELD

This invention relates to the art of physiological measuring. In particular, the invention is a technique for measuring airflow resistance.

BACKGROUND OF THE INVENTION

Airflow resistance is a measurement of a characteristic of an animal which impedes airflow into and out of lungs. Generally, airflow resistance is the quotient of pressure loss and airflow.

A known device for determining airway resistance is shown in U.S. Pat. No. 4,220,161 (Berlin) In this device, a rotating screen includes sections having greater and lesser resistance, and as these sections rotate across a tubular air passage, the pressure and flow rate are perturbed. Airway resistance is calculated by relationships set forth in the patent which are dependent upon variables which can be measured.

The airway perturbation device described in U.S. Pat. No. 4,220,161 and other known resistance measuring devices such as the forced-oscillation technique described in that patent are small-signal devices. That is, the resistance determined by the techniques which generally employ these instruments is an instaneous resistance ordinarily represented by a line tangent to the pressure-flow curve.

The pressure-flow curve is nonlinear, and this presents a problem when using a small-signal device to produce large-signal measurements. For example, a body plethysmograph produces measurements of resistance over pressure and flow variations much larger than that utilized in an airflow perturbation device, and this results in markedly different results. Because the body plethysmograph is a known, standard apparatus, it is desirable to convert measurements made by a small-signal device such as the airflow perturbation device shown in U.S. Pat. No. 4,220,161 to large-signal measurements.

SUMMARY OF THE INVENTION

In accordance with the invention, an airflow perturbation device is used to produce small-signal data which are then used to provide large-signal measurements. In accordance with a preferred embodiment of the invention, measurements of inhalation pressure variation, flow rate variation, and flow rate are made and are combined to provide coefficients. These coefficients are then combined to produce a large-signal airways resistance such as would be produced by a body plethysmograph. The technique may be used for both inhalation and exhalation.

It is an object of this invention to provide a technique for converting small-signal airway resistance measurements to large-signal airway resistance measurements.

Another object of this invention is to provide a technique wherein small-signal airway resistance measurements obtained with an airflow perturbation device may be used to determine values which are in turn used to determine a large-signal airway resistance measurement.

DESCRIPTION OF THE INVENTION

Figure 1:
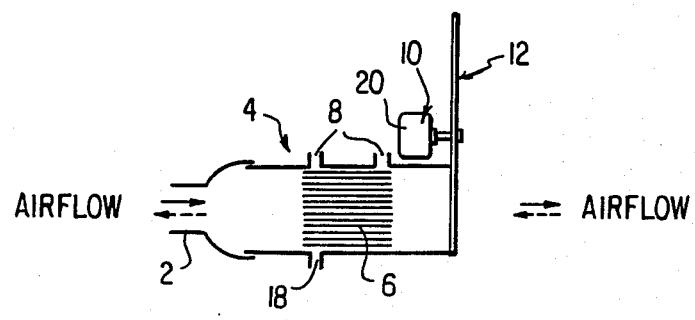
FIG. 1 is a schematic view of a known airflow perturbation device.

With reference to FIG. 1, there is shown a known airflow perturbation device. A patient's mouth (not shown) is connected to an airflow tube 2, through which breathing occurs. A pneumotachometer 4 includes flow-straightening vanes 6 and flow taps 8 for determining the pressure drop thereacross. A motor 10 rotates a screen 12 to vary the airflow resistance and thus perturb the pressure and flow rate of the air flowing through the instrument and into or out of the patient.

Figure 2:
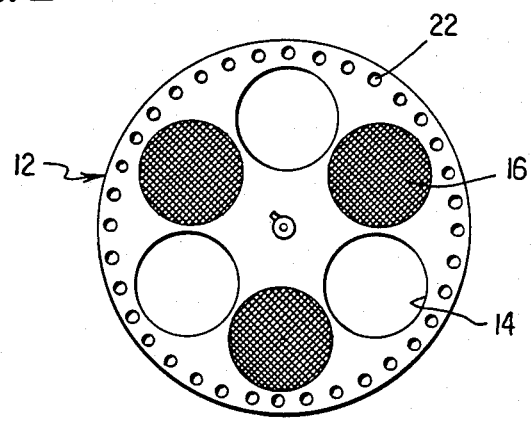
FIG. 2 is a front view of a rotating screen used in an airflow perturbation device such as that shown in FIG. 1.

Screen 12 is shown in more detail in FIG. 2 and includes open sectors 14 and partially blocked sectors 16. The structure shown in FIGS. 1 and 2 is more thoroughly described in an article published in the *IEEE Transactions on Biomedical Engineering*, Vol. BME-31, No. 9, September 1984, the disclosure of which is incorporated by reference.

The instrument shown in FIGS. 1 and 2 produces several measurements. Port 18 allows a measurement of inhalation pressure, output line 20 produces a signal representative of the rate of revolution of screen 12, and frequency calibration holes 22 may be used to provide calibration through an optical or other measuring instrument (not shown).

It will be appreciated that as screen 12 rotates, a flow restriction is imposed which is a small-signal perturbation, preferably at a nominal rate of 10 cps. Preferably, the perturbation produced by screen 12 is approximately sinusoidal, and it will be appreciated by those of skill in the art that instruments of other design will produce such a pressure perturbation.

The determination of inhalation resistance proceeds as follows. A patient breathes through tube 2, inhalation pressure ($p_i$) is measured at port 18 and flow rate ($\dot{V}_i$) is measured by the pressure drop across flow taps 8. As screen 12 rotates, the inhalation pressure and flow rate will be perturbed, and the data may be analyzed to produce the perturbation in inhalation pressure ($\Delta p_i$) and the perturbation in flow velocity ($\Delta \dot{V}_i$). These measurements are used in the following relationship:

$$(\Delta p_i / \Delta \dot{V}_i) = K_1 + 2K_2 \dot{V} + K_2 \Delta \dot{V} + K_3/(V - RV)$$

wherein:

$K_1$, $K_2$, $K_3$ are constants;
$V$ is the lung volume at the time of measurement; and
$RV$ is the residual lung volume.

The residual lung volume may be estimated or determined by a separate instrument in a known manner. Lung volume at the time of measurement may be determined by analyzing the data to numerically integrate the flow rate with respect to time from an exhalation point in which only the residual volume remains in the patient's lung. The remainder of the values, exclusive of the constants, may be easily determined from the data. Constants $K_1$, $K_2$ and $K_3$ are then easily calculated. The value for $\Delta \dot{V}$ is based on a range of past data points and will ordinarily represent an average.

The relationships set forth above are more thoroughly described in "Conversion Between Plethysmograph And Perturbational Airways Resistance Measurements" by Arthur T. Johnson, *IEEE Transactions on Biomedical Engineering*, Vol. BME-33, No. 8, pp. 803-806, August 1986, the disclosure of which is hereby incorporated by reference.

After the constants $K_1$, $K_2$ and $K_3$ have been calculated, large-signal airway resistance may be determined from the relationship $(p_i/\dot{V}_i) = K_1 + K_2\dot{V}_i + K_3/(V - RV)$.

Thus it will be appreciated that the small-signal values determined with the structure shown in FIGS. 1 and 2, or other small-signal measuring devices, may be easily converted into large-signal values.

It will be appreciated that the pressure and flow rate perturbation values from the airway perturbation device vary sinusoidally. The relationship set forth above utilize the in-phase components of these values. One way to obtain the in-phase components is to determine the phase relationship between the pressure and flow variations and to multiply one of the values by the cosine of the phase difference between the curves.

In a preferred embodiment, data is sampled at the rate of 20 samples per perturbation. The data is digitally filtered by passing it through a filter to remove high-frequency noise. The flow perturbation is assumed to coincide with the rotation of wheel 12, and the location of wheel 12 may be easily determined. Once a phase angle is known for any flow perturbation in the set of data, all other phase angles for the flow perturbation are then known.

The data is passed through a low pass filter which retains the base wave form produced by the patient's breathing. If the base wave form slope is too high, the data analyser waits for a base wave form having a smaller slope.

In a manner similar to that described above, airway resistance for exhalation may be determined. The data produced by the airway perturbation device is related as follows to values relevant in determining large-signal exhalation resistance.

$$(\Delta p_e / \Delta \dot{V}_e) = (\Delta \hat{p}_i / \Delta \dot{V}_e + K_4\{1 - (\dot{V}_e + \Delta \dot{V}_e / \dot{V}_L)^n - [1 - \dot{V}_e / \dot{V}_L]^n\} / \Delta \dot{V}_e$$

In this equation, $\Delta p_e$ is the exhalation pressure, $\Delta V_e$ is the variation in exhalation flow rate, $V_e$ is the exhalation flow rate, $V_L$ is the limiting exhalation rate, $K_4$, n are constants, and $\Delta \hat{p}_i$ is the inhalation pressure calculated in accordance with the following relationship.

$$p_i = K_1\dot{V}_i + K_2\dot{V}_i^2 + K_3\dot{V}_i/(V - RV)$$

It will be appreciated that in the above relationship, $\hat{p}_i$ is calculated in accordance with the constants $K_1$, $K_2$ and $K_3$ which are determined as described above with respect to inhalation resistance meaurement.

Once the constants $K_4$ and n are known from the above relationships, large-signal exhalation resistance may be determined from the following relationship.

$$(p_e / \dot{V}_e) = (\hat{p}_i / \dot{V}_e) + [K_4 / \dot{V}_e][(1 - \dot{V}_e / \dot{V}_L)^n - 1]$$

It will be appreciated that a unique technique has been described wherein small-signal measurements may be converted to large-signal measurements. Modifications within the scope of the appended claims will be apparent to those of skill in the art.

What is claimed is:

1. A method for using an instrument which produces a periodic resistance in the airway of an animal to measure the large signal airway resistance comprising applying said instrument to the airway of an animal to perturb the flow of air in said airway, measuring the perturbation in flow rate and the perturbation in pressure caused by said instrument, and ascertaining said large signal airway resistance by determining coefficients from said perturbation in flow rate and said perturbation in pressure.

2. A method according to claim 1 further comprising determining values for flow rate and lung volume and using said flow rate and lung volume values to determine said coefficients.

3. A method according to claim 1 wherein said resistance is inhaling resistance.

4. A method according to claim 1 wherein said resistance is exhaling resistance.

5. A method according to claim 4 further comprising the step of determining the limiting exhalation flow rate and using said limiting exhalation flow rate to determine said coefficients.

6. A method of measuring the large signal airway resistance in an animal comprising periodically perturbing the airflow in the airway of said animal, measuring the small signal pressure variation and the small signal flow rate variation resulting from said perturbation, determining coefficients from said small signal pressure and small signal flow rate variations, and determining the large signal airway resistance from said coefficients.

* * * * *